United States Patent
Hogan et al.

(10) Patent No.: US 7,458,456 B2
(45) Date of Patent: Dec. 2, 2008

(54) PROTECTIVE EYEWEAR

(76) Inventors: Christine K. Hogan, 4130 SW. Woodbury Ct. N., Topeka, KS (US) 66606; Howard E. Hogan, 4130 SW. Woodbury Ct. N., Topeka, KS (US) 66606

(*) Notice: Subject to any disclaimer, the term of this patent is extended or adjusted under 35 U.S.C. 154(b) by 0 days.

(21) Appl. No.: 11/930,684

(22) Filed: Oct. 31, 2007

(65) Prior Publication Data

US 2008/0158504 A1   Jul. 3, 2008

Related U.S. Application Data

(60) Provisional application No. 60/882,316, filed on Dec. 28, 2006.

(51) Int. Cl.
  *A45C 11/04*   (2006.01)
  *G02C 5/08*   (2006.01)

(52) U.S. Cl. .............................. 206/5; 351/63

(58) Field of Classification Search ............ 351/63, 351/41, 158, 45, 46; 206/5, 5.1, 6; 2/15; 128/858; D24/189
See application file for complete search history.

(56) References Cited

U.S. PATENT DOCUMENTS

| | | | |
|---|---|---|---|
| 2,283,752 A | 5/1942 | Gonsett | |
| 2,527,947 A * | 10/1950 | Loos | ........................ 604/294 |
| 2,734,322 A | 2/1956 | Vaughan | |
| 4,093,291 A | 6/1978 | Schurgin | |
| 4,162,542 A | 7/1979 | Frank | |
| 4,642,816 A | 2/1987 | Miller | |
| 4,656,668 A | 4/1987 | Castrejon | |
| 4,701,962 A | 10/1987 | Simon | |
| 4,793,002 A | 12/1988 | Simon | |
| 4,951,658 A | 8/1990 | Morgan et al. | |
| 4,979,811 A | 12/1990 | Boyer | |
| 5,042,649 A | 8/1991 | McNutt | |
| 5,263,200 A | 11/1993 | Miller | |
| D421,124 S | 2/2000 | Yavitz | |
| D425,623 S | 5/2000 | Funk | |
| D429,817 S | 8/2000 | Banks | |
| 6,131,208 A | 10/2000 | Banks | |
| 6,170,664 B1 | 1/2001 | Dar | |
| D440,660 S | 4/2001 | Sternberg | |
| D444,561 S | 7/2001 | Stein | |
| 7,052,130 B2 | 5/2006 | Fishbaugh | |
| 2003/0173234 A1* | 9/2003 | Lin | ............................ 206/5 |

OTHER PUBLICATIONS

Four Seasons Indoor Tanning Catalog; 2007; pp. 177-182.

* cited by examiner

*Primary Examiner*—Hung X Dang
(74) *Attorney, Agent, or Firm*—Hovey Williams LLP

(57) ABSTRACT

Eyewear includes a pair of lenses and a case. A first lens includes a first face and a second face, and a second lens includes a second lens face. The second lens is adapted to nest with the first lens when the second lens face is in register with and placed against the first face of the first lens. The case houses the first lens and the second lens when the second lens is nested with the first lens, wherein the first lens is adapted to nest with the case.

24 Claims, 2 Drawing Sheets

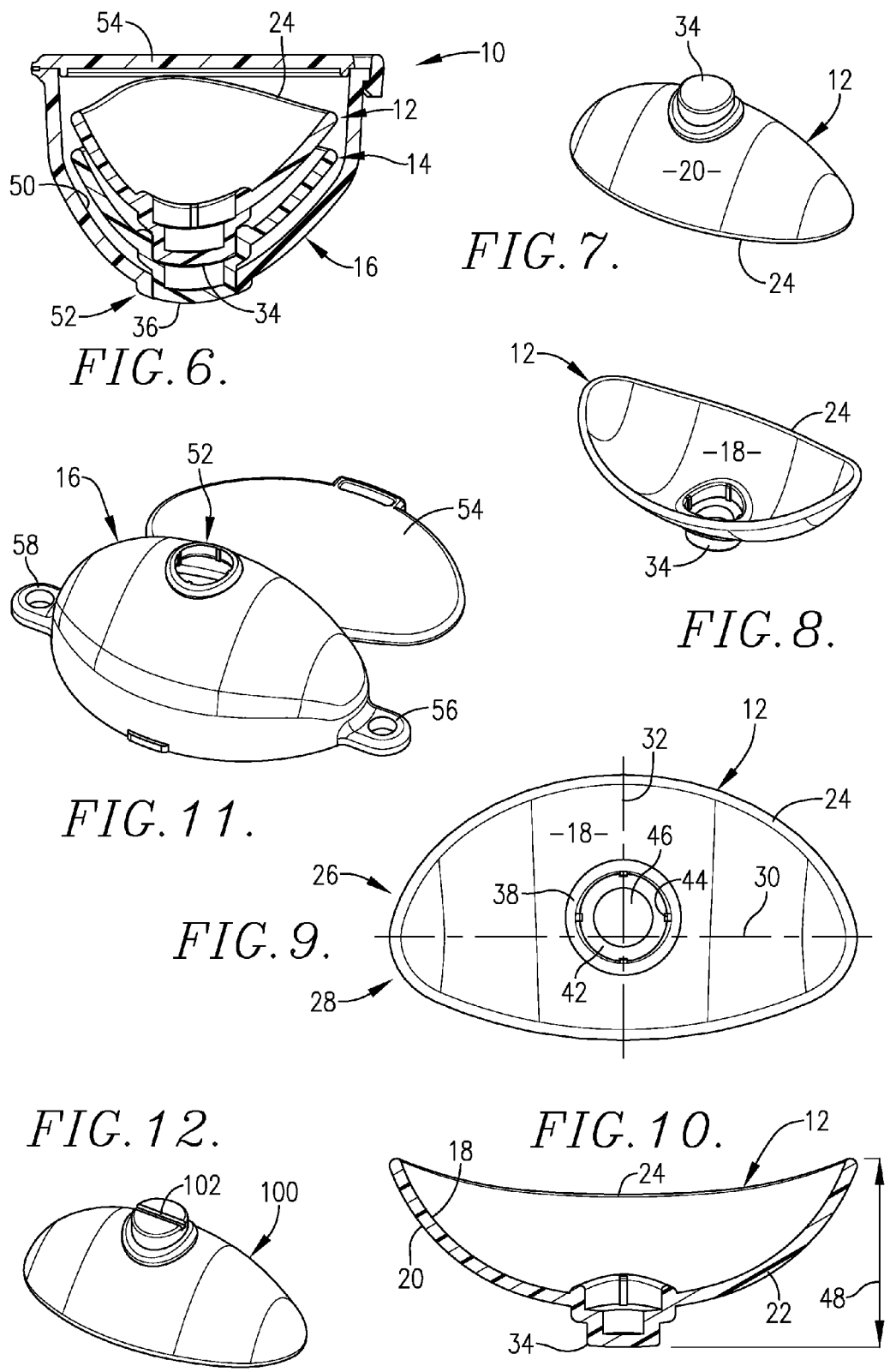

PROTECTIVE EYEWEAR

RELATED APPLICATION

This application is a non-provisional patent application claiming priority benefit of copending U.S. Provisional Patent Application No. 60/882,316, titled "Eye Socketz", filed Dec. 28, 2006, incorporated by reference herein.

BACKGROUND

1. Field

Embodiments of the present invention relate to eyewear. More particularly, embodiments of the present invention relate to protective lenses for use during tanning or similar activities that are adapted to be conveniently and securely stored and transported between uses.

2. Related Art

While tanning, whether in a tanning booth or exposed to natural sunlight, it is often desirable to use protective eyewear to limit the amount of light that reaches a user's eyes. Conventional sunglasses may effectively limit the amount of light reaching the user's eyes, but may also have an undesirable effect on tanning. The frames and lenses of the sunglasses, for example, may prevent certain portions of the user's face from tanning, resulting in an undesirable tan pattern. For this and other reasons, pairs of individual protective lenses, each lens adapted to cover an eye of the user, have been adopted to minimize the unnecessary shading of the user's face during tanning and thus the undesirable tan pattern. Unfortunately, individual lenses are relatively small and may be inadvertently separated or lost between uses.

SUMMARY

Embodiments of the present invention address the above-mentioned limitations and provide a distinct advance in the art of eyewear. More particularly, embodiments of the invention provide a pair of lenses that are adapted to be conveniently and securely stored and transported between uses.

According to a first embodiment, a first lens includes a first face and a second face, and a second lens includes a second lens face. The second lens is adapted to nest with the first lens when the second lens face is placed proximate the first face of the first lens. A case houses the first lens and the second lens when the second lens is nested with the first lens, wherein the first lens is adapted to nest with the case.

According to a second embodiment, a first lens presents a first attachment element and a second lens presents a second attachment element. The second attachment element connects to the first attachment element, thereby removably securing the first lens to the second lens in a nested relationship. A case houses the first lens and the second lens when the first lens is secured to the second lens in the nested relationship.

According to a third embodiment, a first protective lens presents a first substantially semi-ellipsoidal shape and includes a first attachment element proximate an apex thereof. A second protective lens presents a second substantially semi-ellipsoidal shape substantially identical to the first semi-ellipsoidal shape of the first protective lens. The second protective lens includes a second attachment element proximate an apex thereof for connecting to the first attachment element by way of a friction fit, to thereby removably secure the first protective lens to the second protective lens in a nested relationship. A concave face of the first protective lens mates with a convex face of the second protective lens when the first attachment element is connected to the second attachment element.

A case houses the first protective lens and the second protective lens when the first and second lenses are connected in the nested relationship, the case presenting a third attachment element for connecting to the first attachment element, thereby removably securing the first protective lens within the case. A convex face of the first protective lens mates with an inner concave surface of the case when the first protective lens is removably secured to the case.

According to a fourth embodiment of the invention, a method of using eyewear comprises separating a first lens from a second lens by applying a separating forcing to the first lens and the second lens, thereby disengaging a first attachment element of the first lens from a second attachment element of the second lens. The method further comprises placing the first lens over a first eye and placing the second lens over a second eye, removing the first lens from the first eye and the second lens from the second eye, and attaching the first lens to the second lens by placing the first lens over the second lens in a nested relationship and applying a joining pressure to the first lens and the second lens, thereby urging the first attachment element into engagement with the second attachment element.

A fifth embodiment of the invention is a method of using eyewear comprising removing a pair of nested protective lenses from a case by applying pressure to a first attachment element of a first lens via an aperture of the case, separating a first protective lens of the pair of nested protective lenses from a second protective lens of the pair of nested lenses by applying a separating forcing to the first lens and the second lens, and placing the first lens over a first eye and placing the second lens over a second eye. The method further comprises removing the first lens from the first eye and the second lens from the second eye, attaching the first lens to the second lens by placing the first lens over the second lens in a nested relationship and applying a joining pressure to the first lens and the second lens, thereby urging the first attachment element into engagement with the second attachment element. The first lens is attached to the protective case by placing the first lens against a mating surface of the case and urging the second attachment element into engagement with the third attachment element.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the preferred embodiments and the accompanying drawing figures.

BRIEF DESCRIPTION OF THE DRAWING FIGURES

A preferred embodiment of the present technology is described in detail below with reference to the attached drawing figures, wherein:

FIG. 1 is a top perspective view of a lens case housing a pair of nested lenses, illustrating a cover of the case in a closed position thereby hiding the pair of nested lenses;

FIG. 2 a bottom perspective view of the case of FIG. 1, illustrating a portion of an attachment element of one of the lenses engaging an aperture of the case;

FIG. 6 is a side elevation sectional view of the case and lenses of FIG. 1;

FIG. 7 is a perspective view of one of the lenses of FIG. 1 illustrating a convex face of the lens;

FIG. 8 is a perspective view of the lens of FIG. 7 illustrating a concave face of the lens;

FIG. 9 is a plan view of the lens of FIG. 7 illustrating the concave face of the lens;

FIG. 10 is a front elevation sectional view of the lens of FIG. 7;

FIG. 11 is a bottom perspective view of the case of FIG. 1 without the lenses, illustrating the cover in an open position; and FIG. 12 is a perspective view of a lens constructed according to an alternative embodiment, the lens including a receptacle for engaging a retaining component such as a retaining band.

Figure 1:
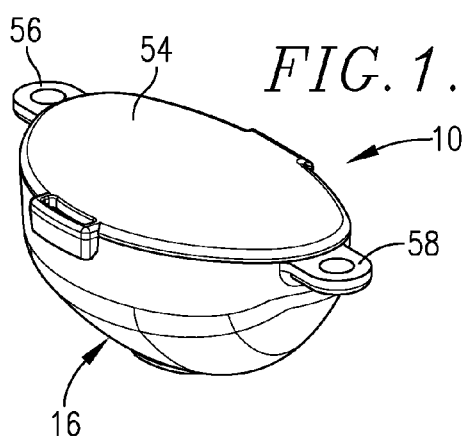
Figure 2:
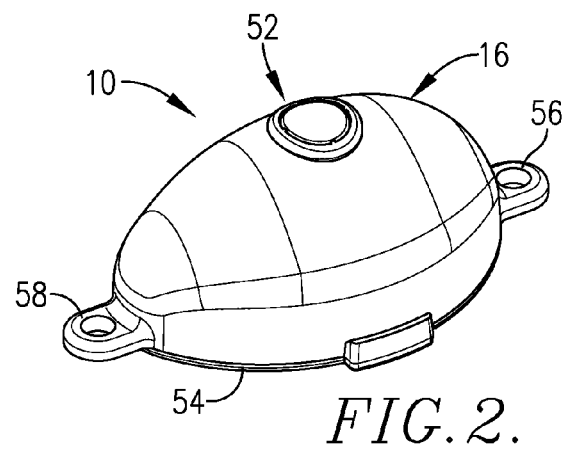
Figure 3:
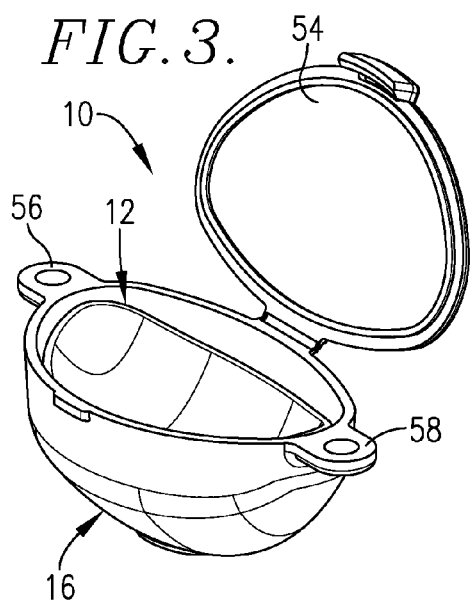
FIG. 3 is a top perspective view of the case of FIG. 1, illustrating a cover of the case in an open position revealing the lenses nested within the case.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the present technology references the accompanying drawings that illustrate specific embodiments in which the technology may be practiced. The embodiments are intended to describe aspects of the technology in sufficient detail to enable those skilled in the art to practice the invention. Other embodiments can be utilized and changes can be made without departing from the scope of the present teachings. The following detailed description is, therefore, not to be taken in a limiting sense. The scope of the present invention is defined only by the appended claims, along with the full scope of equivalents to which such claims are entitled.

An eyewear assembly constructed according to principles of the present technology is illustrated in FIGS. 1-6 and designated generally by the reference numeral 10. The eyewear assembly 10 broadly includes a first lens 12, a second lens 14, and a case 16.

Referring also to FIGS. 7-10, the first lens 12 is illustrated in greater detail. The first lens 12 and the second lens 14 may be identical or substantially identical in form and function, therefore aspects of the lens 12 are described herein with the understanding that the lens 14 includes similar or identical aspects. The lenses 12,14 may be protective lenses, such as lenses used to limit or eliminate the light reaching a user's eyes during tanning. While the lenses 12,14 will be generally described herein as protective lenses, it will be appreciated that the present teachings are not so limited and that other types of lenses are within in the ambit of the present invention. By way of example, the lenses 12,14 may alternatively or additionally be prescription lenses.

The lens 12 is generally adapted to be used with a user's eye (not shown) to minimize the amount of light reaching a user's eye, such as where the user is tanning and the user's face is exposed to a substantial amount of light. The lens 12 thus presents a shape and size that allow the lens 12 to fit on or over one of the user's eyes and to cover a minimal portion of the eye. The lenses 12 and 14 are adapted to be disconnected and separated one from the other such that the user can individually place the first lens 12 over a first eye and the second lens 14 over a second eye.

The lens 12 generally presents an elongated cup or bowl shape with an inner concave surface 18 and an outer convex surface 20. More particularly, the lens 12 may be defined by a main wail 22 that may be partially ellipsoidal in shape, such as semi-ellipsoidal, and has a rim 24. As illustrated in the plan view of FIG. 9, the rim 24 presents a first portion 26 and a second portion 28 separated by a longitudinal axis 30, wherein each portion 26,28 generally corresponds to a portion of an ellipse. The first portion 26 extends further from the major axis 26 than the second portion 28, resulting in the major axis 26 being offset from a center of a lateral axis 32 of the rim 24. The rim 24 may be contoured (as illustrated) along the longitudinal axis 30, the lateral axis 32, or both to conform to a user's eye or face.

The illustrated longitudinal axis 30 generally corresponds to a line connecting the two most distal points of the rim 24, and the illustrated lateral axis 32 is perpendicular to and bisects the longitudinal axis 30. A length of the lens 12 corresponding to the distance from a first point of the rim 24 and a second point of the rim 24 along the longitudinal axis 30 may be within the range of from about 2.0 cm to about 6.0 cm and more preferably within the range of from about 3.0 cm to about 5.0 cm. More particularly, the length may be about 3.7 cm, about 4.0 cm, or about 4.3 cm. A width of the lens 12 corresponding to the distance from a first point of the rim 24 to a second point of the rim 24 along the lateral axis 32 may be within the range of from about 0.5 cm to about 3.5 cm and more preferably within the range of from about 1.0 cm to about 2.0 cm. More particularly, the width may be about 1.6 cm, about 2.0 cm, or about 2.4 cm.

Figure 5:
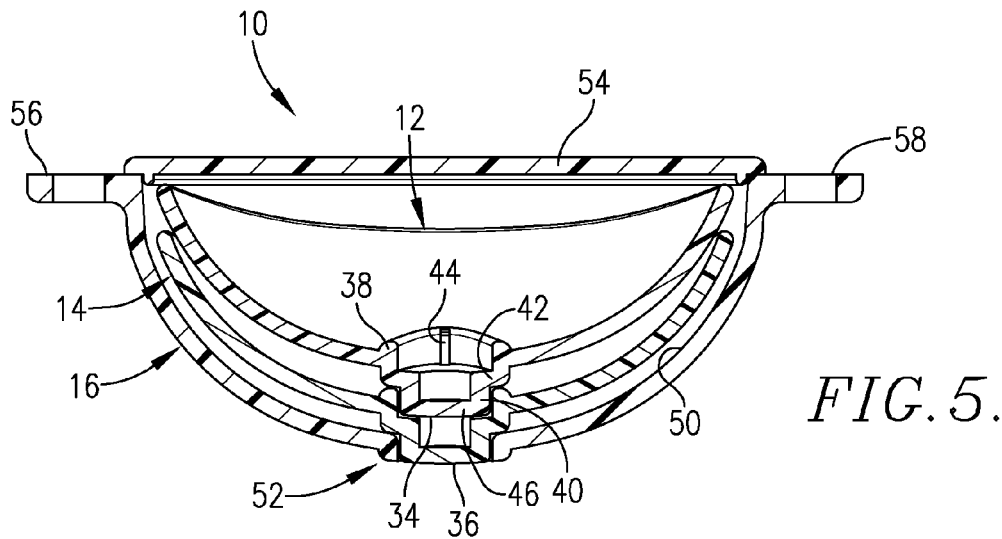
FIG. 5 is a front elevation cross sectional view of the case and lenses of FIG. 1.

A first attachment element 34 is located at or proximate to an apex of the main wall 22 of the first lens 12, and a second attachment element 36 is correspondingly located at or proximate to an apex of the second lens 14. The attachment elements 34,36 are adapted to enable attaching one of the first lens 12 and the second lens 14 to the other. The attachment elements 34,36 may be located on the lenses 12,14 such that when the lenses 12,14 are stacked in a nested fashion (as illustrated in FIGS. 5 and 6), the first attachment element 34 is in register with the second attachment element 36. Thus, the first attachment element 34 engages the second attachment element 36 when the lenses 12,14 are nested so that the lenses 12,14 are removably attached and remain in the nested relationship until the user forces them apart.

The attachment elements 34,36 may include interlocking male and female portions. By way of example, the attachment elements 34,36 may each include a recessed portion defined in part by a pair of telescopingly offset, concentric, cylindrical walls extending substantially normally to the main wall 22. An inboard cylindrical wall 38 is generally larger in diameter than an outboard cylindrical wall 40, wherein a shoulder 42 separates the inboard wall 38 from the outboard wall 40. An inner surface of the inboard cylindrical wall 38 presents one or more ribs 44 for facilitating engagement of the first and second attachment elements 34,36, as explained below in greater detail. The one or more ribs 44 may generally run up and down, as illustrated in FIG. 5, or alternatively may run along a different direction, including left to right. An outer end wall portion 46 completely or partially caps the outboard cylindrical wall 40.

With reference to FIG. 10, a height 48 of the lens 12 corresponds to a vertical distance between a lowest point and a highest point of the side elevation view of the lens 12. The height 48 may be within the range of from about 0.5 cm to about 3.5 cm and more preferably within the range of from about 1.0 cm to about 3.0 cm. More particularly, the depth 48 may be about 1.7 cm, about 2.0 cm, or about 2.3 cm.

The case 16 is adapted to house the first lens 12 and the second lens 14 when the lenses 12,14 are nested as illustrated in FIGS. 5 and 6. The case 16 includes an inner concave surface 50 that generally corresponds in shape to the convex surface of the lens 14 such that when the lenses 12,14 are housed in the case 16, the lenses 12,14 nest in or seat against the inner concave surface of the case 16.

The case 16 may include an attachment element 52 that is generally in register with the attachment elements of the lenses 12,14 when the lenses 12,14 are housed in the case 16. The attachment element 52 of the case 16 may include an aperture that is adapted to engage one or both of the inboard cylindrical wall 38 and the outboard cylindrical wall 40 of either the first lens 12 or the second lens 14. As illustrated in FIG. 5, the outboard cylindrical wall of the second lens 14 at least partially extends into the aperture of the attachment element 48 and engages an edge of the wall defining the aperture, securing the lens 14 to the case 16 by way of a friction fit. When the attachment element of the lens 14 is thus engaged with the attachment element 48 of the case 16, the attachment element of the lens 14 is at least partially exposed to an outside of the case 16 via the aperture of the case 16. This configuration provides a means of removing the lenses 12,14 from the case 16 wherein a user simply applies pressure to the exposed portion of the second attachment element 36 via the aperture of the attachment element 52 to force disengagement of the lens 14 and the case 16.

The case 16 may include a removable or pivoting cover 54 for selectively sealing the case 16 to prevent dust and other debris from entering the case 16 and to prevent the lenses 12,14 from inadvertently falling out of the case 16. The case 16 may also include one or more eyelets 56,58 or similar structural elements for supporting the case 16 by connecting, for example, to a key ring, a key chain, a bracelet and so forth.

The case 16 may be small enough to conveniently fit within a user's pocket or purse. A volume occupied by the case 16 may be, for example, within the range of from about 10.0 cm to about 27.0 cm, more preferably within the range of from about 12.0 cm to about 25.0 cm, even more preferably within the range of from about 14.0 cm to about 23.0 cm. More particularly, the volume may be about 16.0 cm, about 18.0 cm, or about 21.0 cm.

The case 16 may by constructed of a substantially rigid material, such as plastic, nylon, wood, or metal, or may be constructed of a substantially malleable material, such as an elastomer. If the case 16 is constructed of a substantially malleable material, the lenses 12,14 may be removed by pressing on a portion of the case 16 opposite the cover 54, thereby causing the case 16 to deform and pushing the lenses 12,14 out of the case 16.

Figure 4:
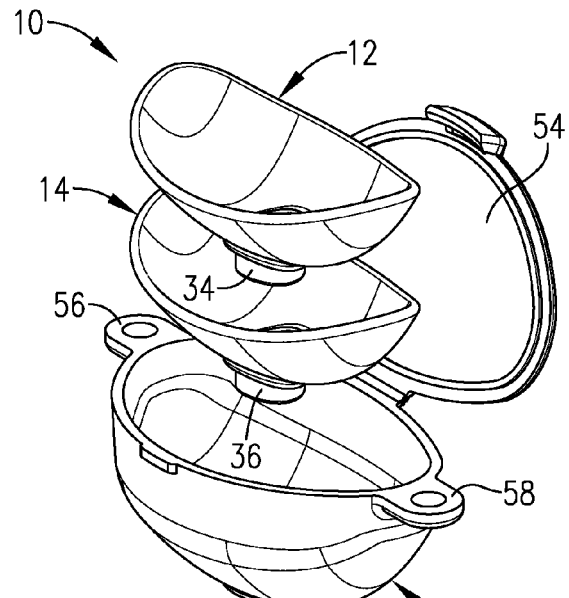
FIG. 4 is an exploded top perspective view of the case and lenses of FIG. 1, illustrating a first lens and a second lens removed from the case and separated by a space.

In use, the first lens 12 and the second lens 14 are stored in the case 16 by attaching one to the other. More particularly, the lenses 12,14 are nested by aligning the lenses 12,14, as illustrated in FIG. 4, stacking the lenses 12,14 on against the other, and then urging one of the first and second attachment elements 34,36 into engagement with the other. As illustrated in FIGS. 5 and 6, the first attachment element 34 engages the second attachment element 36 when an outer surface of the outboard cylindrical wall 40 of the first attachment element 34 frictionally engages the ribs and/or the inner surface of the inboard cylindrical wall of the second attachment element 36.

The lenses 12,14 may then be placed in the case 16. The convex surface 20 of the lens 12 is aligned with the inner concave surface of the case 16 and the attachment element of the lens 12 is urged into engagement with the attachment element of the case 16 such that the lens 12 is seated against the inner concave surface of the case 16. At this point, the lenses 12,14 are secured in place in the case 16 and the door of the case 16 is closed to further protect the lenses 12,14.

To remove the lenses 12,14 from the case 16, the user opens the door of the case 16 and dislodges the lenses 12,14 from the case 16 by applying pressure on the second attachment element 36 that is exposed to the outside of the case 16 via the aperture. Once the attachment element 36 of the lens 14 is separated from the attachment element 52 of the case 16, the lenses 12,14 fall free of the case 16. The lens 12 is then separated from the lens 14 by applying a separating force to the lenses 12,14 to disengage the first attachment element 34 and the second attachment element 36. With the lenses 12,14 free, they are placed over the user's eyes.

A lens 100 is illustrated in FIG. 12 and is constructed according to an alternative embodiment of the present technology. The lens 100 may be identical to the lenses 12,14 described above, except that the lens 100 includes a receptacle 102 for engaging a retaining component, such as a chord, string, or band, that secures the lens 100 to the user's face. The illustrated receptacle 102 includes a groove located on an end wall portion of the lens 100 that is similar to the end wall portion 46 described above in relation to the lens 12. An opening of the groove may by narrower than a seat of the groove to enable the retaining element to snap into place.

Although the invention has been described with reference to the embodiments illustrated in the attached drawing figures, it is noted that equivalents may be employed and substitutions made herein without departing from the scope of the invention as recited in the claims. For example, the particular form or function of the various attachment elements is not important to the present technology, and the attachment elements may present alternative shapes and sizes with equally-preferred results.

Having thus described various embodiments of the invention, what is claimed as new and desired to be protected by Letters Patent includes the following:

1. Eyewear comprising:
    a first lens including a first face and a second face;
    a second lens including a second lens face, wherein said second lens is adapted to nest with said first lens when said second lens face is placed proximate said first face of said first lens; and
    a case for housing said first lens and said second lens when said second lens is nested with said first lens, wherein said first lens is adapted to nest with said case.

2. The assembly as set forth in claim 1, wherein said first lens has a first shape and said second lens has a second shape that is substantially identical to said first shape.

3. The assembly as set forth in claim 1, wherein said first lens and said second lens each includes a receptacle for engaging a retaining component for securing said lenses against a user's face.

4. The assembly as set forth in claim 1, wherein said first face of said first lens is concave and said second lens face is convex.

5. The protective eyewear as set forth in claim 1, wherein said case is adapted to house said first lens and said second lens only when said second lens is nested with said first lens.

6. The protective eyewear as set forth in claim 1, wherein said case is at least partially constructed of an elastomer.

7. Eyewear comprising:
a first lens presenting a first attachment element;
a second lens presenting a second attachment element for connecting to said first attachment element to thereby removably secure said first lens to said second lens in a nested relationship; and
a case for housing said first lens and said second lens when said first lens is secured to said second lens in said nested relationship.

8. The eyewear as set forth in claim 7, wherein said first lens has a first shape and said second lens has a second shape that is substantially identical to said first shape.

9. The eyewear as set forth in claim 7, wherein said case further includes a third attachment element for connecting to said second attachment element thereby removably securing said second lens in said case.

10. The eyewear as set forth in claim 9, wherein said third attachment element includes an aperture for removably receiving said second attachment element in a friction fit, wherein said aperture extends from an inside of said case to an outside of said case.

11. The eyewear as set forth in claim 9, wherein said case is adapted to house said first lens and said second lens only when said first lens is connected to said second lens in said nested relationship.

12. The eyewear as set forth in claim 9, wherein said first attachment element is located proximate a center of said first lens and said second attachment element is located proximate a center of said second lens.

13. The eyewear as set forth in claim 9, wherein said case is at least partially constructed of an elastomer.

14. The protective eyewear as set forth in claim 7, wherein said first lens and said second lens each includes a receptacle for engaging a retaining component for securing said lenses against a user's face.

15. Protective eyewear comprising:
a first protective lens presenting a first substantially semi-ellipsoidal shape and including a first attachment element proximate an apex thereof;
a second protective lens presenting a second substantially semi-ellipsoidal shape substantially identical to said first semi-ellipsoidal shape of said first protective lens, said second protective lens including a second attachment element proximate an apex thereof for connecting to said first attachment element by way of a friction fit to thereby removably secure said first protective lens to said second protective lens in a nested relationship, wherein a concave face of said first protective lens mates with a convex face of said second protective lens when said first attachment element is connected to said second attachment element; and
a case for housing said first protective lens and said second protective lens when said first and second lenses are connected in said nested relationship, said case presenting a third attachment element for connecting to said first attachment element thereby removably securing said first protective lens within said case, wherein a convex face of said first protective lens mates with an inner concave surface of said case when said first protective lens is removably secured to said case.

16. The protective eyewear as set forth in claim 15, wherein said first attachment element includes a recessed portion and said second attachment element includes a protuberance adapted to mate with said recessed portion of said first attachment element and attach thereto via a friction fit.

17. The protective eyewear as set forth in claim 16, wherein said first attachment element and said second attachment element each include a first cylindrical wall and a second cylindrical wall, wherein said first cylindrical wall of said first attachment element defines said recessed portion and said second cylindrical wall of said second attachment element defines said protuberance.

18. The protective eyewear as set forth in claim 16, said case further including an eyelet for supporting said case.

19. The protective eyewear as set forth in claim 15, said first attachment element and said second attachment element each including an outer end wall with a groove therein for receiving a retaining component.

20. A method of using eyewear, said method comprising:
separating a first lens from a second lens by applying a separating forcing to said first lens and said second lens thereby disengaging a first attachment element of said first lens from a second attachment element of said second lens;
placing said first lens over a first eye and placing said second lens over a second eye;
removing said first lens from said first eye and said second lens from said second eye; and
attaching said first lens to said second lens by placing said first lens over said second lens in a nested relationship and applying a joining pressure to said first lens and said second lens, thereby urging said first attachment element into engagement with said second attachment element.

21. The method as set forth in claim 20, further comprising removing said first lens and said second lens from a case by applying pressure to a first attachment element of said first lens via an aperture of said case.

22. The method as set forth in claim 21, further comprising attaching said first lens to said protective case by placing said first lens against an internal surface of said case and urging said second attachment element into engagement with a third attachment element of said case.

23. The method as set forth in claim 20, wherein said first attachment element is located proximate a center of said first lens and said second attachment element is located proximate a center of said second lens.

24. A method of using eyewear, said method comprising:
removing a pair of nested protective lenses from a case by applying pressure to a first attachment element of a first lens via an aperture of said case;
separating a first protective lens of said pair of nested protective lenses from a second protective lens of said pair of nested lenses by applying a separating forcing to said first lens and said second lens;
placing said first lens over a first eye and placing said second lens over a second eye;
removing said first lens from said first eye and said second lens from said second eye;
attaching said first lens to said second lens by placing said first lens over said second lens in a nested relationship and applying a joining pressure to said first lens and said second lens, thereby urging said first attachment element into engagement with said second attachment element; and
attaching said first lens to said protective case by placing said first lens against a mating surface of said case and urging said second attachment element into engagement with said third attachment element.

* * * * *